(12) United States Patent
Khanuja et al.

(10) Patent No.: US 6,420,174 B1
(45) Date of Patent: Jul. 16, 2002

(54) METHOD OF PRODUCING ORGANOGENETIC TISSUE FROM A PLANT OF THE GENUS MENTHA

(75) Inventors: Suman Preet Singh Khanuja; Ajit Kumar Shasany; Sunita Dhawan; Mahendra Pandurang Darokar; Tiruppadiripuliyur Ranganathan Santha Kumar; Dharmendra Saikia; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/536,379

(22) Filed: Mar. 28, 2000

(51) Int. Cl.$^7$ .................................................. C12N 5/00
(52) U.S. Cl. .................... 435/430.1; 435/155; 435/420; 435/430
(58) Field of Search ................................ 435/420, 410, 435/430, 430.1, 155

(56) References Cited

U.S. PATENT DOCUMENTS 5,466,455 A * 11/1995 Huffstutler et al.
5,898,001 A * 4/1999 Kumar et al.

* cited by examiner

*Primary Examiner*—Leon B. Lankford, Jr.
(74) *Attorney, Agent, or Firm*—Birch, Stewart, Kolasch & Birch, LLP

(57) ABSTRACT

The present invention is related to a method of producing organogenetic tissues from a plant of the genus Mentha, said method comprising the steps of culturing an explant from a plant of genus Mentha on an initiation medium in the presence of 400 to 600 lux light at a temperature of 23–27° C., with 16 hours of photoperiod, to obtain calli, transferring the calli to a basal medium comprising minerals and vitamins to ensure development of shoots, and culturing the shoots in a medium substantially free of growth hormones and containing menthol in a concentration of about 80 μg ml$^{-1}$ to ensure root formation.

8 Claims, 3 Drawing Sheets

(3 of 3 Drawing Sheet(s) Filed in Color)

METHOD OF PRODUCING ORGANOGENETIC TISSUE FROM A PLANT OF THE GENUS MENTHA

FIELD OF INVENTION

The invention relates to a method for regeneration of mentha plants from cell or tissue culture through organogenesis. More particularly, the invention relates to the use of menthol for the development of plant parts through organogenesis from calli in hormone free media.

BACKGROUND OF THE INVENTION

The essential oil of *Mentha arvensis* Linn. var Piperascens is a well known source of the monoterpene 'menthol' used in the cosmetics, pharmaceutical, food, confectionery and liquor industries. The biosynthesis of menthol in the plant has a complex cascade fashion of genetic regulation during plant differentiation. Specific oil glands (trichomes) formed on the surface of the leaf and stem isolate these toxic monoterpenoid products to prevent the cellular damage. Monoterpenes are also known to be cytotoxic to plant tissues by acting through inhibition of respiration and photosynthesis, by drastically affecting the mitochondria, golgi bodies etc. and decreasing cell membrane permeability.

However, the present invention is to an experimental chance encounter while screening menthol tolerant clones of *Mentha arvensis* in tissue culture in presence of menthol in the medium. The applicants have developed a method for screening high menthol yielding genotypes in vitro in presence of menthol. While carrying out this large scale screening procedure, the applicants planned to subject the callus directly to menthol selection for selection tolerant clones. During this process, the applicants observed that menthol at toxic concentration induced the callus (transferred from other media) to form high frequency quality shoots better than those induced in presence of normally used growth hormones for shoot regeneration. This invention inspite of being simple may have far reaching consequences as a number of plants produce secondary metabolites causing end product toxicity and those upon testing may also be useful for organogenesis replacing the growth hormones.

In the present invention, the applicants observed that a lethal concentration of this toxic monoterpene (menthol) in medium induced *Mentha arvensis* callus (developed from other media), produced better quality shoots with much higher frequency than when induced by the normal growth hormones, contrary to the general observation that Mentha plants die when cultured in a medium containing menthol in toxic concentrations. There is no report of replacement of growth hormones by a monoterpene for inducing organogenesis from callus.

OBJECTS OF THE INVENTION

Therefore, the main object of the invention is to provide a method of regeneration of mentha plants from cell or tissue culture through organogenesis. Another object of the invention is to provide a method in which the use of menthol for the development of plant parts through organogenesis from calli in hormone free media is successfully carried out. Yet another object of the invention is to provide a novel and unique use of menthol as growth promoter, inducer of shoot regeneration and signal transducer, which can be provided in the hormone free culture medium for induction of shoots from undifferentiated mass of cells of *Mentha arvensis*.

SUMMARY OF THE INVENTION

Accordingly, the present invention provide's a method for the development of plants and plant parts through organogenesis from calli upon culturing in media comprising menthol in toxic concentrations.

DETAILED DESCRIPTION

Accordingly, the invention provides a novel and unique procedure of in vitro organogenesis from callus developed from any tissue culture media and then transferring it to medium free from growth hormones but containing menthol at a toxic concentration, wherein a. the said callus is undifferentiated mass of cells, b. the said toxic concentration is the concentration at which the regenerated shoots die which is 80 $\mu g \, ml^{-1}$ or more in *Mentha arvensis*, c. the said menthol is produced from the essential oil of the plant of genus Mentha or synthesised chemically, and d. the said growth hormones are but not limited to auxin, 1-napthalene acetic acid and cytokinin, benzyl aminopurine.

Another embodiment of the invention provides a method of producing organogenetic tissues from a plant of the genus Mentha, said method comprising the steps of:

(i) culturing an explant from a plant of genus Mentha in a initiation medium in the presence of 400 to 600 lux light at a temperature of 23–27° C., with 16 hours of photoperiod, to obtain calli, (ii) transferring the calli to a basal medium comprising minerals and vitamins to ensure development of shoots, and (iii) culturing the shoots in a medium substantially free of growth hormones and containing menthol in a concentration of about 80 $\mu g \, ml^{-1}$ to ensure root formation.

The preferred initiation medium employed, in the present invention is modified after MS medium, additionally comprising 0.2 $\mu g \, ml^{-1}$ of auxins selected from naphthalene acetic acid or 1-NAA and 5 $\mu g \, ml^{-1}$ of a cytokinin selected from BAP or benzyl aminopurine.

In another embodiment the invention provides a novel and unique use of menthol as growth promoter, inducer of shoot regeneration and signal transducer, which can be provided in the hormone free culture medium for induction of shoots from undifferentiated mass of cells of *Mentha arvensis* wherein a. the menthol can replace the growth hormones for organogenesis wherein organogenesis comprises induction of differentiation from differentiated tissue like callus, and b. the frequency of shoots generated is more in comparison to medium containing growth hormones.

The invention is described in detail hereafter with reference to the accompanying drawings following examples and FIG. 1, which are provided merely to illustrate the invention. Various modifications that may be apparent to one skilled in the art are deemed to fall within the scope of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Response of callus in different media

The applicants earlier developed a protocol for screening high menthol yielding plants by inoculating the in vitro raised somaclones in medium containing toxic concentrations of menthol in the tissue culture medium (Patent pending). In this procedure, screening of 2850 variants yielded 30 clones surviving 70 $\mu$g ml$^{-1}$ of menthol concentration in the medium out of which only 5 stable clones could be isolated which were of high menthol content type in comparison to the parent variety 'Himalaya' (U.S. Pat No. PP 10935). Increasing the menthol concentration further killed all the shootlets. At this point, the applicants planned experiments to subject the callus directly to menthol selection instead of the regenerated shoots to save on time, space and labour. The logic was to isolate the tolerant cell lines if any, growing from this callus later.

The plant variety used in these experiments was cv. Himalaya (U.S. Pat No. PP10935) of *Mentha arvensis* L. (2n=96). The suckers of *M. arvensis* L. cv. Himalaya for multiplication of the plant material and future experimentation were obtained from CIMAP's gene bank. For callus production, the explant material was collected from the field grown plants and surface sterilized by washing sequentially with 2% detergent, distilled water containing a few drops of Savlon (Johnson and Johnson, India), 0 1% acidified mercuric chloride and autoclaved distilled water before inoculation. About 1 cm long internode pieces were inoculated in the Murashige and Skoog medium (Murashige T, Skoog F; 1962. A revised medium for rapid growth and bioassay with tobacco tissue cultures. Physiol Planta, 15:473–497) supplemented with 0.2 $\mu$g ml$^{-1}$ of an auxin (NAA, 1-napthalene acetic acid) and 5 $\mu$g ml$^{-1}$ of a cytokinin (BAP, benzyl aminopurine). The cultures were grown at 25±2° C. and 400 to 600 lux light intensity with 16 h photoperiod. The green callus mass developed from the cut ends was taken for further experimentation.

Figure 1:
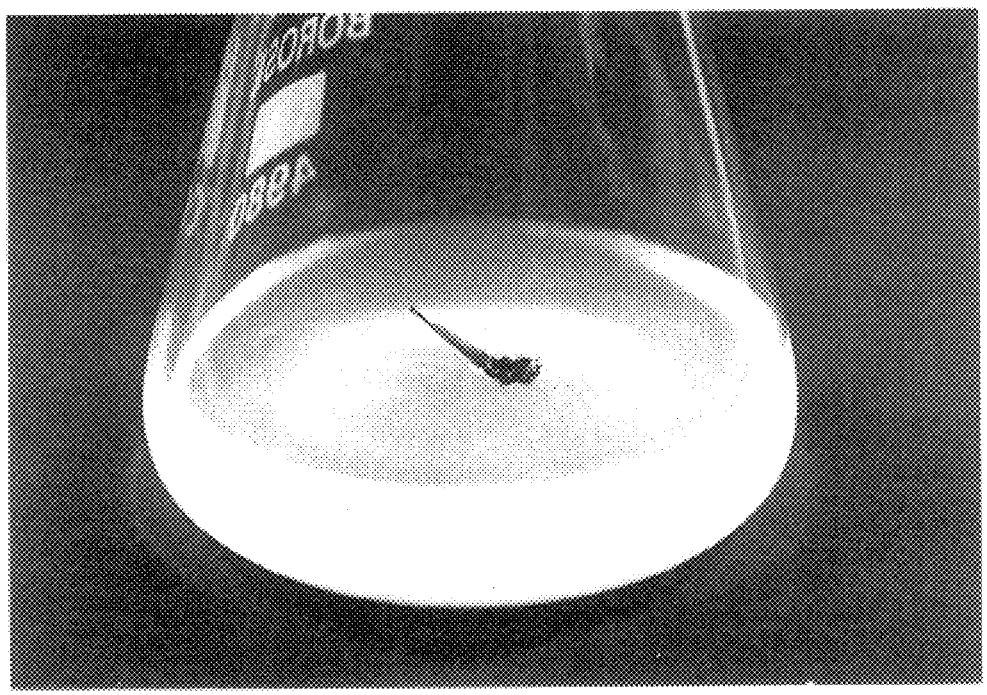
FIG. 1. Callus in MSO medium after 10 days.
Figure 2:
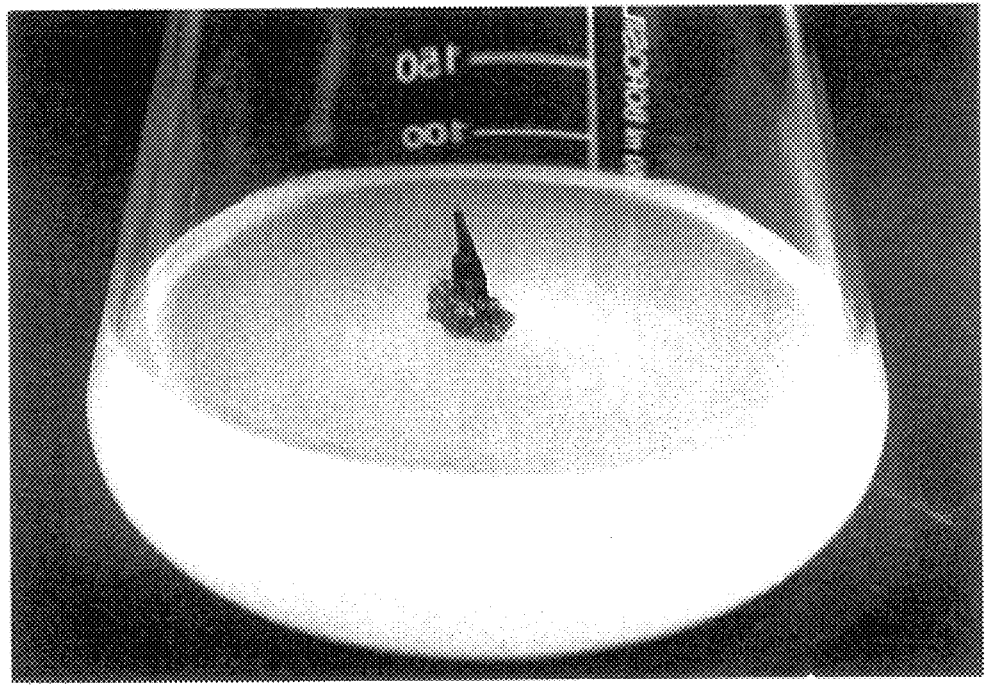
FIG. 2. Shoot primodia induction from callus in MSA-2 medium after 10 days.
Figure 3:
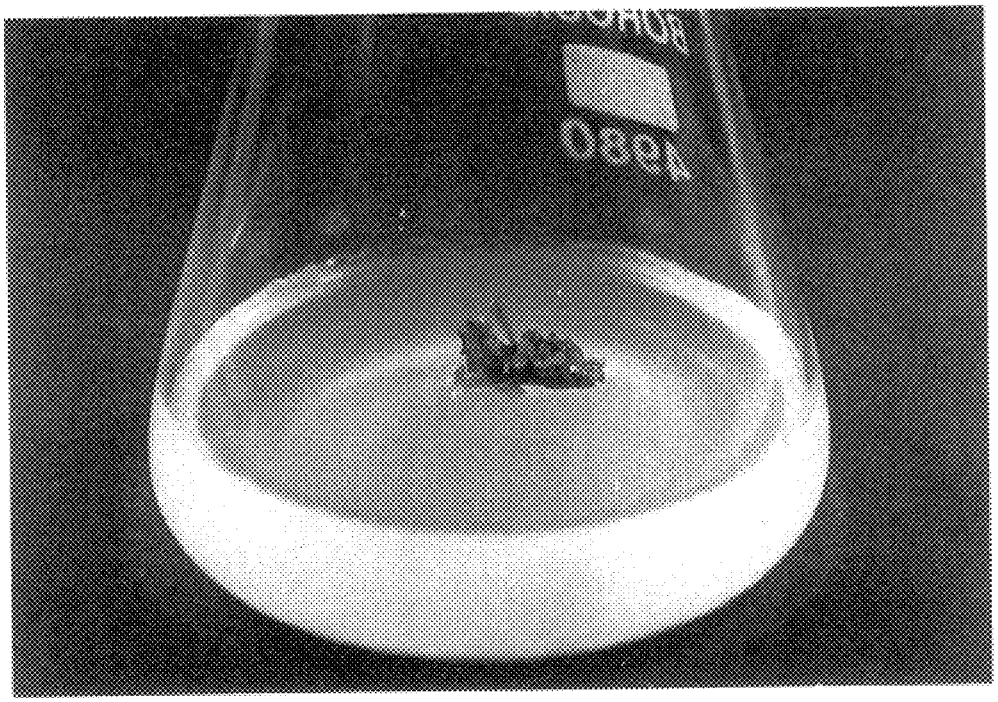
FIG. 3. Shoot primodia induction from callus in MT-80 medium after 10 days.
Figure 4:
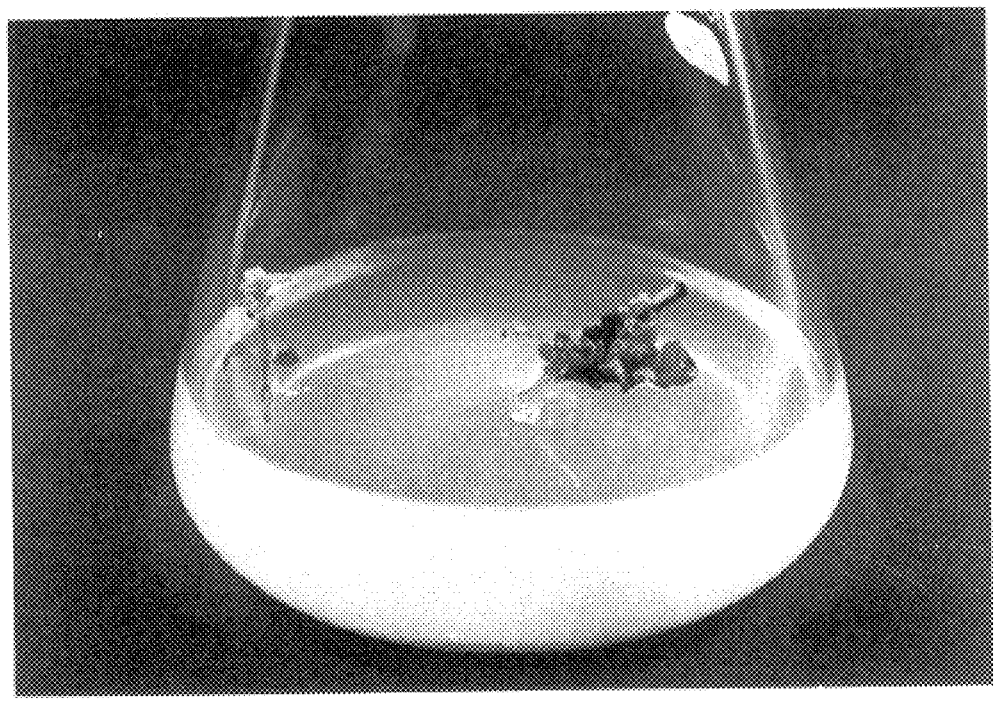
FIG. 4. Death of regenerated shoot (left) and induction of organogenesis from callus (right) in MT-80 medium after 20 days, and FIG. 5. Shoots developed in MSA-2 medium (left), in MT-80 (right) and fate of regenerated shoots on MT-80 control flask (middle).
Figure 5:
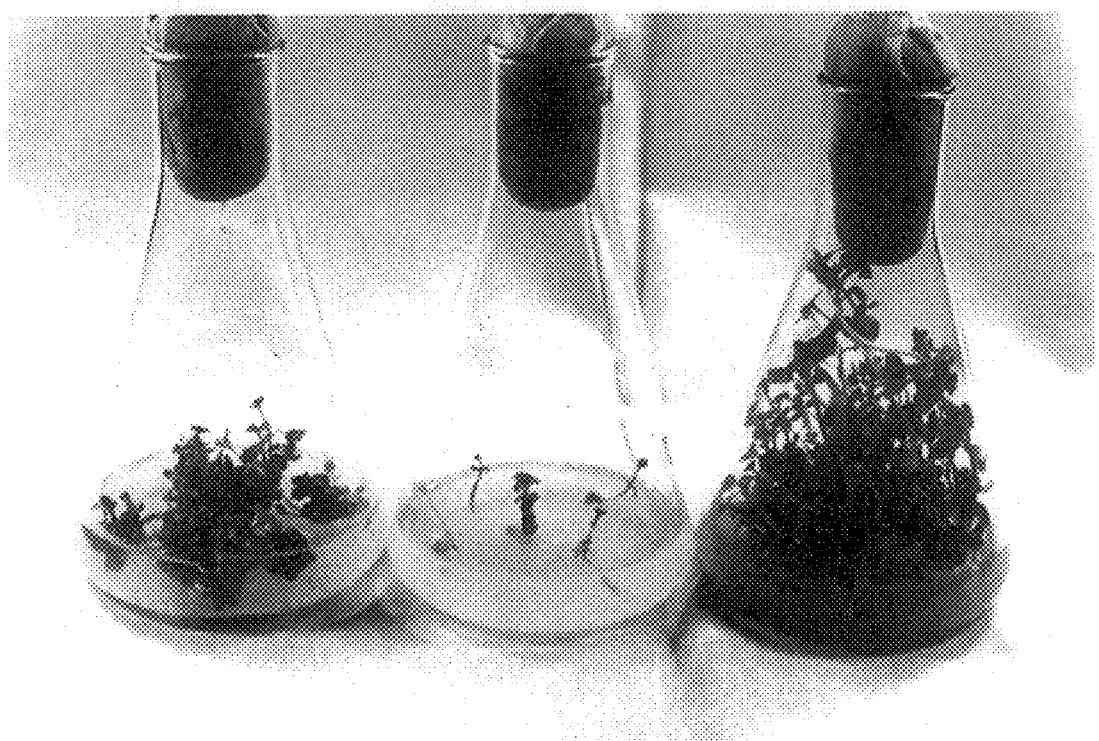

In the next phase, the callus was sub cultured in three different media: i) the basal medium MSO containing only the vitamins and minerals without any growth hormones; ii) MSA-2 medium which is MSO with 0.2 $\mu$g ml$^{-1}$ concentration of NAA and 5 $\mu$g ml$^{-1}$ of a cytokinin BAP; and iii) MT-80 medium which is MSO with only 80 $\mu$g ml$^{-1}$ menthol. On each kind of these media, an independent callus (50 mg) or 5 independently regenerated shoots were inoculated per flask in 5 replications each. The experiment was conducted in the completely randomized design (CRD) fashion. Cultures were incubated and maintained at 25±2° C. and 400–600 lux light intensity with 16-hour photoperiod. The response was recorded every 24 hours over a period of one week and then weekly upto one month. The results, which clearly demonstrated the novel use of menthol in proficient induction of organogenesis from callus in a hormone free medium, are described in FIG. 1 and the examples below.

EXAMPLE 1

Effect of Menthol in the Medium on Individual Shoots

When the regenerated shoots of 2 to 2.5 cm long were inoculated in the basal medium, all of them started producing root primodia which ultimately gave rise to well develop roots. But on MSA-2 medium after 7 days, the cut ends of the shoots swelled, which then converted to a green callus mass after 15 days and ultimately started regenerating into shoots. However, all the shoots inoculated into the MT 80 medium) died within 7 days upon wilting and the process was irreversible (Table 1).

TABLE 1

Response of regenerated shoots in different media

| | Response observed when regenerated shoots were inoculated in | | |
|---|---|---|---|
| No of days | MSO | MSA-2 | MT-80 |
| 7 | Root primodia from cut end | Swelling from the cut end | Shoots died |
| 14 | Conspicuous rooting | Green callus from cut end | Shoots died |
| 21 | Increased root length, shoot growth | Regeneration from the cut end | Shoots died |

EXAMPLE 2

Effect of Menthol in the Medium on Callus

The transferred callus pieces did not respond when inoculated into MSO medium even after 21 days. On the MSA-2 medium the callus showed regeneration of shoots as expected (Table 2). But most interestingly, on the MT-80 medium, which is the MS basal medium with menthol (80 $\mu$g ml$^{-1}$), concentration the frequency of induction of shoot regeneration was significantly higher than MSA-2 medium which contain growth hormones for shoot induction and growth. This observation (FIG. 1)was surprising as the shoot induction from the same callus is not supported by the basal medium but supported by the same basal medium when menthol is supplemented. Thus, the experiment was repeated three times and the same repeatable response was observed. Menthol not only induced shoot regeneration but also the frequency of induction was much higher than the induction by the growth hormones.

TABLE 2

Shooting response of callus in different media

| | Number of shoots primodia initiated when callus was inoculated into | | |
|---|---|---|---|
| No of days | MSO | MSA-2 | MT-80 |
| 0 | 0 | 0 | 0 |
| 7 | 0 | 6.8 + 0.1 | 16.0 + 1.4 |
| 15 | 0 | 14.8 + 0.1 | 22.8 + 1.3 |
| 21 | 0 | 17.2 + 0.1 | 26.0 + 0.8 |

EXAMPLE 3

Effect of Menthol on other Explants and Regeneration

At this stage, the applicants wanted to know whether any other parts of the plant (explants) show similar response as callus and lead to direct regeneration. In the same experimental design we inoculated different parts of the plant in different media and the observations were recorded after 7 and 15 days. Invariably, all these explants on MT-80 showed chlorophyll loss, wilting and browning leading to total mortality (Table 3) where as the responses in media without menthol were as expected.

tiated mass of cells called callus, about 1.0 cm long internode pieces are inoculated in the Murasighe and Skoog medium containing 0.2 $\mu g\ ml^{-1}$ concentrations of an auxin (NAA, 1-napthalene acetic acid) and 5 $\mu g\ ml^{-1}$ of a cytokinin (BAP, benzyl aminopurine). The cultures are grown at 25±2° C. and 400 to 600 lux light intensity with 16 h photoperiod for 15 days. The green calluses

TABLE 3

Response of other explants in different media

| Medium | Leaf discs | | Root pieces | | Internodes | |
|---|---|---|---|---|---|---|
| | 7 days | 15 days | 7 days | 15 days | 7 days | 15 days |
| MSO | No change | No change | No change | No change | No change | No change |
| MSA-2 | Curling of leaf discs from cut ends | Callusing or green growth initiated. | No change (normal) | No change (normal) | Swelling initiated from cut ends. | Green callus growth |
| MSO + 60 ppm menthol | Green leaf pieces. | Slight browning or wilting. | No change | Browning from cut ends. | Green | Wilting started and chlorophyll loss from cut ends |
| MSO + 70 ppm menthol | Wilting started from cut ends | Browning and chlorophyll loss | No change | Wilting started | Green | Wilting of internodes |
| MSO + 80 ppm menthol | Wilting from cut ends | Chlorophyll loss | Wilting | Wilting | Wilting | Browning and chlorophyll loss |

EXAMPLE 4

Characteristics and Growth of Menthol Induced Shoots

Following continued observations on the regenerated shoots in comparative manner, we observed that the menthol-induced shoots were more vigorous in growth compared to the shoots growing on other media. The leaves were also larger in the shoots regenerated on the medium containing 80 $\mu g\ ml^{-1}$ of menthol (Table 4).

TABLE 4

Dimension of leaves in the regenerated shoots

| MSO | | MSA-2 | | MT-80 | |
|---|---|---|---|---|---|
| Leaf length | Leaf breadth | Leaf length | Leaf breadth | Leaf length | Leaf breadth |
| 1.40 + 0.03 | 1.20 + 0.05 | 1.45 + 0.08 | 1.30 + 0.07 | 2.26 + 0.06 | 1.70 + 0.07 |

The above examples of experimentation made it quite apparent that the secondary metabolite 'menthol' produced by mint plant *Mentha arvensis* can induce differentiation of the callus tissue towards regeneration at a toxic concentration which otherwise kills the regenerated shoots and other explants. This invention is astonishing and has far reaching consequences considering the number of such secondary metabolites in plants. In this invention, we have developed a procedure and established the novel use and importance of secondary metabolite 'menthol' to replace the growth hormones in vitro for shoot induction from callus. Further, we expect menthol might be involved in some kind of signal transduction in vivo during specific stages of growth and development in specific tissues of the plant.

Protocol
1. Explant is inoculated in the artificial medium aseptically and incubated for the time sufficient to form undifferentiated mass developed from the cut ends are then taken for shoot induction.
2. The callus pieces are transferred to the medium without any growth hormones but containing menthol at a toxic concentration otherwise lethal to the differentiated tissue. In this experiment the callus developed were transferred to the MSO medium containing menthol at a concentration of 80 $\mu g\ ml^{-1}$. The callus on this medium shows visible shoot induction within 7 to 10 days.

We claim:
1. A method of producing organogenetic tissues from a plant of the genus Mentha, said method comprising the steps of:
   (i) culturing an explant from a plant of genus Mentha in an initiation medium in the presence of 400 to 600 lux light at a temperature of 23–27° C., with 16 hours of photoperiod, to obtain calli,
   (ii) transferring the calli to a basal medium comprising minerals and vitamins to obtain shoots, and
   (iii) culturing the shoots in a medium substantially free of growth hormones and containing menthol in a concentration of about 80 $\mu g\ ml^{-1}$.
2. A method as claimed in claim 1, wherein the initiation medium is modified after MS medium, additionally comprising (a) 0.2 $\mu g\ ml^{-1}$ of auxins selected from the group consisting of naphthalene acetic acid and 1-NAA and (b) 5 µg ml$^{-1}$ of a cytokinin selected from BAP and benzyl aminopurine.

3. A method for in vitro organogenesis from callus comprising developing callus from any tissue culture media; and then transferring said developed callus to a medium free from growth hormones but containing menthol at a toxic concentration, wherein:

(a) said callus is an undifferentiated mass of cells, and (b) said toxic concentration is the concentration at which the regenerated shoots die which is 80 µg ml$^{-1}$ or more in *Mentha arvensis*.

4. The method as claimed in claim 3, wherein said menthol is produced from essential oil of a plant of genus Mentha or synthesized chemically.

5. The method as claimed in claim 3, wherein said growth hormone is selected from the group consisting of auxin, 1-napthalene acetic acid, cytokinin and benzyl aminopurine.

6. A method for inducing growth of shoots from a callus of *Mentha arvensis*, comprising culturing said callus in a medium free from growth hormone but containing menthol in a concentration of 80 µg/ml or more.

7. A method for inducing shoot regeneration from a callus of *Mentha arvenis*, comprising:

culturing said callus in a medium free from growth hormone but containing menthol in a concentration of 80 µg/ml or more.

8. A method for inducing differentiation from an undifferentiated callus of *Mentha arvenis* comprising culturing said callus in a medium free from growth hormone but containing menthol in a concentration of 80 µg/ml or more.

* * * * *